United States Patent [19]
Steinberg et al.

[11] Patent Number: 5,427,762
[45] Date of Patent: Jun. 27, 1995

[54] PROCESS FOR THE CONVERSION OF CARBONACEOUS FEEDSTOCKS TO PARTICULATE CARBON AND METHANOL

[75] Inventors: Meyer Steinberg, Melville; Edward W. Grohse, Port Jefferson, both of N.Y.

[73] Assignee: Hydrocarb Corporation, Port Jefferson Station, N.Y.

[21] Appl. No.: 209,605

[22] Filed: Mar. 9, 1994

Related U.S. Application Data

[63] Continuation of Ser. No. 852,910, Mar. 18, 1992, abandoned, which is a continuation of Ser. No. 424,594, Oct. 20, 1989, abandoned, which is a continuation-in-part of Ser. No. 54,610, May 27, 1987, abandoned.

[51] Int. Cl.$^6$ .............................................. C01B 31/02
[52] U.S. Cl. .............................. 423/449.1; 423/449.8; 423/450; 423/454
[58] Field of Search ............... 432/449, 450, 454, 445; 515/202; 44/502, 607, 90; 423/449.1, 449.8

[56] References Cited

U.S. PATENT DOCUMENTS

| | | | |
|---|---|---|---|
| 2,138,249 | 11/1938 | Wilcox | 423/454 |
| 3,676,070 | 7/1972 | Vanderveen et al. | 423/450 |
| 3,984,519 | 10/1976 | Dolci et al. | 423/449 |
| 4,045,092 | 8/1977 | Keller | 44/51 |
| 4,185,083 | 1/1980 | Walker | 423/449 |
| 4,203,915 | 5/1980 | Supp et al. | 518/712 |
| 4,247,530 | 1/1981 | Cheng et al. | 423/449 |
| 4,339,546 | 7/1982 | Randalls | 518/702 |
| 4,476,250 | 10/1984 | Jayner et al. | 518/715 |
| 4,623,668 | 11/1986 | Broecker et al. | 518/709 |

FOREIGN PATENT DOCUMENTS

2086389  5/1984  United Kingdom ............... 518/702

OTHER PUBLICATIONS

Steinberg, "Production of a Clean Carbon Fuel Derived From Coal For Use in A Stationary . . . ", Proceeding of Coal Slurry Fuels Preparation and Utilization, 8th Conf. Fla., May 1986 pp. 291-302.

Veziroglu et al "Hydrogen Systems" vol. II, Internation Symposium on Hydrogen Systems, May 1985 Beijing, China 217-228.

Hydrocarb-M Process for Conversion of Coals to a Carbon-Methanol Liquid Fuel (Carboline-M), Meyer Steinberg and Edward W. Grohse, Brookhaven National Laboratory (BNL-43569), Jan. 1989.

Coal to Methanol to Gasoline by the Hydrocarb Process, Meyer Steinberg, Brookhaven National Laboratory (BNL-43555), Aug. 1989.

*Primary Examiner*—Robert M. Kunemund
*Attorney, Agent, or Firm*—Philip C. Strassburger

[57] ABSTRACT

A process for the production of a pollutant-free particulate carbon (i.e., a substantially ash-, sulfur- and nitrogen-free carbon) from carbonaceous feedstocks. The basic process involves de-oxygenating one of the gas streams formed in a cyclic hydropyrolysis-methane pyrolysis process in order to improve conversion of the initial carbonaceous feedstock. De-oxygenation is effected by catalytically converting carbon monoxide, carbon dioxide, and hydrogen contained in one of the pyrolysis gas streams, preferably the latter, to a methanol co-product. There are thus produced two products whose use is known per se, viz., a substantially pollutant-free particulate carbon black and methanol. These products may be admixed in the form of a liquid slurry of carbon black in methanol.

1 Claim, 3 Drawing Sheets

PROCESS FOR THE CONVERSION OF CARBONACEOUS FEEDSTOCKS TO PARTICULATE CARBON AND METHANOL

STATEMENT OF GOVERNMENT INTEREST

The United States Government has certain rights in this invention pursuant to Contract Number DE-AC02-76CH00016, awarded by the United States Department of Energy.

This is a continuation of U.S. application Ser. No. 07/852,910, filed Mar. 18, 1992, now abandoned, which was a continuation of U.S. application Ser. No. 07/424,594, filed Oct. 20, 1989, now abandoned which is a continuation-in-part application of U.S. application Ser. No. 07/054,610, filed May 27, 1987, now abandoned which are incorporated by reference herein.

FIELD OF THE INVENTION

This invention relates to an improved process for the extraction of carbon from carbonaceous materials, to its isolation as a substantially pure, ash-, sulfur- and nitrogen-free particulate carbon useful as a fuel as well as an improved substitute for currently available carbon blacks, and to the economical co-production of methanol therewith. It further relates to such a process which may be directly utilized for the production of a pumpable non-polluting liquid fuel comprising a mixture of particulate carbon and methanol that can be burned in heat engines, steam generators, boilers and the like and which can also be used as a replacement for conventional, more expensive, and polluting petroleum-derived liquid fuels.

BACKGROUND OF THE INVENTION

In the past, the methods used for the production of carbon black have largely been determined by the availability of inexpensive fossil fuels for energy and raw material requirements therein, and by the intended use of the carbon black product, whether as a pigment in ink or the like, or as a rubber-additive in the manufacture of automotive tires, etc. In recent years, the fossil fuels of choice, because of availability and price, have been primarily residual oils, petroleum tars, coal tars, and natural gas.

Three methods of producing carbon black have been dominant: the oldest of these, the channel process, is a low efficiency conversion method in which natural gas-fueled flames are impinged upon a relatively cool surface.

In the second method, the furnace combustion process (the most widely used at present), carbon black for the rubber industry is produced by the combustion and cracking of a mixture of oil and air. This process has a conversion efficiency about four to five times that of the channel process.

The third method, the furnace thermal process, provides in the neighborhood of 10% of the present production of carbon black. That process has a carbon conversion efficiency approximately twice that of the furnace combustion process. It involves the intermittent heating of a furnace filled with ceramic checkerwork to cracking temperatures. The furnace is heated by the combustion with air of natural gas or petroleum and/or hydrogen produced in the thermal decomposition of such materials to carbon black. The flow of air is then terminated without discontinuing the flow of fuel; thermal decomposition of the hydrocarbon fuel is thus effected, with the concomitant formation of carbon black.

The realization that the supply of gaseous and liquid fossil fuels is limited and that the cost of such fuels can never decrease, has spurred interest in research into methods for the economic production of non-polluting fuels from carbonaceous feedstocks such as coal, char, coke, natural gas, wood and other cellulosic materials, municipal solid wastes, and agricultural products. Most of such research has centered on the manufacture of substitute natural gas (SNG) and synthetic liquid hydrocarbon fuels from coals of various ranks. These processes invariably require the separate manufacture of large quantities of hydrogen required as a reactant.

The results of some of the foregoing research efforts have been described in the patent literature, e.g., in Schora U.S. Pat. No. 3,861,885, which describes a process for producing a pollutant-free carbon black solid fuel useful as feed for coal-fired turbines, as an additive to diesel fuel, and as a material for pipelining to areas where air pollution requirements dictate a fuel with low sulfur content. This process involves the initial pretreatment of coal to remove a hydrocarbon stream, followed by gasification of the resulting devolatilized coal to yield a product gas that is essentially carbon monoxide and hydrogen, followed by cooling the product gas under controlled conditions in a fluidized bed to precipitate carbon black in a finely divided state.

Johnson U.S. Pat. No. 3,424,556 discloses a method of producing carbon black from coal, involving the initial decomposition of the coal to tar, ash, and gaseous hydrocarbons, followed by dehydrogenation of the tar hydrocarbons and aggregation of the carbon. Cheng et al. U.S. Pat. Nos. 3,975,504; 4,072,468; and 4,206,175 similarly describe the formation of carbon black by utilizing hot combustion gases to cause pyrolytic decomposition of coal or a hydrocarbon feed, the hot combustion gases being produced by the oxidation of a carbonaceous fuel.

In present commercial processes for the manufacture of carbon black (thermal black) from natural gas, a substantial fraction of the carbon black produced is recovered from a hot hydrogen-rich gas phase by spray cooling with industrial water and collection of the cooled carbon black from the bottom of the spray cooling apparatus. The remainder of the carbon black product is recovered from the refractory-lined walls of the carbon black reactors. The carbon black thus produced tends to be contaminated with hardness from the cooling water employed, and possibly with other impurities adsorbed during collection from the spray-cooling equipment or during the subsequent separation from the cooling water, as well as with refractory material from the reactor walls.

The preceding, more recent examples of the prior art, all use an oxygen-containing gas to react with a carbonaceous material as a step in the production of particulate carbon black, in contrast to the former profligate, partial combustion and thermal decomposition of natural gas.

The preparation of methane by the hydropyrolysis of coal has also been disclosed in the prior art. Hence, Ullman et al. U.S. Pat. No. 4,597,776 describes the treatment of a hydrogen-deficient carbonaceous material with a hydrogen-containing pyrolysis gas at an elevated temperature and pressure to produce a product gas mixture comprising methane, carbon monoxide and hydrogen. This product gas mixture is enriched with a specified concentration of hydrogen by contacting it with a controlled amount of steam in a water-gas shift reaction zone to react at least a portion of the carbon monoxide to produce hydrogen. The resulting hydrogen-rich gas mixture is cryogenically separated into its constituent parts, and a mixture comprising hydrogen, carbon monoxide, and methane, is combined with a controlled amount of steam and recycled.

One of the present inventors has also suggested the preparation of pollutant-free particulate carbon by pyrolyzing coal or other carbonaceous material to methane, followed by thermally decomposing the methane to a particulate carbon. See "The Direct Use of Natural Gas (Methane) For Conversion of Carbonaceous Raw Materials to Fuels and Chemical Feedstocks", presented at the International Symposium on Hydrogen Systems, held in Beijing, China, on May 7-11, 1985 ("Hydrogen Systems", Vol. II, Edited by T. N. Veziroglu et al, pp. 217-228). The cited paper does not disclose the specific manner in which such a process may be carried out.

In parent application Ser. No. 54,610, filed May 27, 1987, the present inventors have disclosed a specific technique for combining the exothermic hydropyrolysis of carbonaceous materials to methane with the endothermic decomposition of the resulting methane to produce a pollutant-free particulate carbon. In the process described therein, the methane-rich gas stream produced by the hydropyrolysis reaction is de-oxygenated by a dewatering operation, preferably recuperatively wherein most of the thermal energy removed during pre-cooling of the humid gas prior to condensation is returned to the process during reheating of the dewatered gas, thereby facilitating high carbon conversion efficiencies in the subsequent methane pyrolysis reaction. By interposing the de-oxygenating step as described, a commercially feasible process for converting carbonaceous feedstocks to particulate carbon black is provided.

Alternatively, the hydrogen-rich gas stream exiting from the methane pyrolysis reactor can be similarly de-oxygenated to enhance carbon conversion efficiencies, but in the cases considered to date, deoxygenating the methane-rich gas exiting from the hydropyrolysis reactor is more effective. As discussed below in connection with the present invention, the reverse is true when deoxygenation is performed by means of the production and recovery of methanol (instead of by the condensation and withdrawal of water.)

The separate manufacture of hydrogen is not required in the process of the aforesaid parent application Ser. No. 54,610 since the ultimate primary product, particulate carbon, contains no hydrogen. Moreover, as described hereinafter, in the process of the present invention sufficient hydrogen and oxygen are frequently present in the carbonaceous feedstock being processed to permit the co-production of substantial quantities of the secondary co-product, methanol, without requiring the addition of extra hydrogen.

It is, therefore, among the objects of the present invention to provide a further improved process for the conversion of carbonaceous feedstocks to substantially pollutant-free particulate carbon or carbon blacks. A further object of the invention is to provide such a process which directly produces, in addition to such carbon blacks, methanol, separately or in combination with the carbon blacks as a novel non-polluting liquid fuel.

SUMMARY OF THE INVENTION

In accordance with this invention, an improved process is provided for the production of pollutant-free particulate carbon (i.e., substantially ash-, sulfur- and nitrogen-free carbon), from a carbonaceous feedstock. Like the invention of the aforesaid parent application, the present invention involves de-oxygenating one of the gas streams formed in a cyclic hydropyrolysis/methane-pyrolysis process in order to improve conversion of the carbonaceous feedstock. In the present process, however, the de-oxygenation is primarily effected by catalytically combining hydrogen and carbon monoxide (and also carbon dioxide if present in significant concentrations) in one or the other of the pyrolysis gas streams to a methanol co-product. There are thus produced two valuable products whose use is known per se, viz., a substantially pollutant-free particulate carbon black and methanol.

The only evident possible sources of contamination of carbon black produced by the process of the present invention are (1) that resulting from possible attrition or fragmentation of the particulate refractory material being recirculated and (2) possible adsorption of contaminant gases and/or condensation, during cooling of the carbon black, of ash constituents which were volatile at the temperature of operation of the reactor systems.

Contamination due to attrition of the recirculated refractory particulates is minimized by the use of hard, smooth, vitrified non-porous spheres or particles such as of alumina ($Al_2O_3$) and relatively gentle transport of same under conditions of dense phase incipient or quiescent fluidization as opposed to the relative violent action (promotive of attrition and fragmentation) inherent in the use of pneumatic solids transport employing high gas velocities.

Contamination caused by adsorption of contaminant gases or condensation of volatile ash constituents during cooling of the carbon black can be minimized or avoided by careful, hot inert gas purging of the contaminants from the hot carbon black prior to attempting to cool the carbon black. Essentially pure particulate carbon, carbon black, is produced by the process hereof; the particulate carbon black of the invention is thus of greater purity than the carbon black presently produced commercially.

In accordance with a further feature of the process hereof, both of these products may be formed in admixture with one another, i.e., in the form of a slurry of from about 10 to 90%, preferably from about 25 to 75%, by weight of the pollution-free carbon particles comprising generally spherical particles of diameters of the order of about 0.02 to 10 microns, in methanol. This new product may be used directly as a premium liquid fuel.

When, in accordance herewith, a carbonaceous feedstock is hydropyrolyzed in an excess of hydrogen, the oxygen in the feedstock, including that in any associated moisture, shows up in the gaseous reaction stream as primarily carbon monoxide and water vapor. The resulting carbon monoxide (along with lesser to trace amounts of carbon dioxide) diluted with hydrogen, constitutes a synthesis gas which, following desulfurization, is fed to a conventional methanol catalyst conversion zone to convert the diluted carbon monoxide and carbon dioxide to methanol. At the same time, use of the catalytic conversion step de-oxygenates the process stream in order to provide efficient carbon deposition. The oxygen is thus removed as a valuable clean fuel or chemical commodity, i.e., methanol, rather than merely as water.

The conventional method for producing methanol involves the steam reforming of natural gas or the partial oxidation of petroleum residues. See, for example, the *Encyclopedia of Chemical Technology*, Kirk and Othmer, 3rd Ed., Vol. 15, pp 398–415, McGraw-Hill, New York, N.Y. (1981) and *Industrial Chemicals*, Faith, Keyes and Clark, 4th Ed., pp. 524–29, John Wiley & Sons, New York, N.Y. (1975). Processes for the production of methanol from coal via conventional gasification of the latter are also becoming of increasing interest, although thus far much less widely practised. The foregoing processes yield a synthesis gas ($CO+CO_2+2H_2$) from which methanol is catalytically produced.

The prior art processes thus form a single product, methanol, as distinguished from the carbon and methanol co-products formed by the process of the present invention. Further, the prior art steam reforming or steam-oxygen gasification techniques require more processing steps than the process hereof, and thus necessitate higher capital investment. Additionally, higher efficiencies of conversion of carbonaceous feedstocks to carbon and methanol are obtained in the present process than in presently known processes. Accordingly, substantial economies are achieved by using the process of the invention.

The required selling price of methanol produced from coal by conventional gasification techniques (including the necessary return of investment) includes the costs of gasification of coal and the formation of a synthesis gas of composition suitable for economic catalytic conversion of the latter to methanol. Thus, the lowest price of methanol presently produced from coal in the United States (assuming the price of coal is at $25.00/ton) is about $0.50/gallon. Even by reforming natural gas priced at only $2.00/thousand standard cubic feet, the required price of methanol so produced would not be less than about $0.40/gallon.

It is estimated that the cost of co-producing carbon black and methanol by the process of the present invention is about $0.14/gallon methanol, assuming the carbon black is sold at $2.50/million Btu. Even if the plant cost assumed in the above calculations were doubled, the product cost would only be $0.21/gallon methanol, considerably less than that of methanol currently produced or projected.

It is interesting to note that in 1986, the California State Energy Commission obtained a quotation from a Middle East source to deliver methanol to the West Coast of the United States at a price as low as $0.25/gallon. This price is based on the throwaway cost of flared gas associated with foreign crude oil production. Accordingly, the price of methanol produced by the present process is even lower than the Mideast delivered price to the United States quoted several years ago. This result is due, in part, to the fact that the present integrated process produces both carbon black and methanol at high process efficiencies.

It may be added that, employing lower grade subbituminous or lignite coals having high oxygen contents, there is sufficient oxygen to produce the desired amount of methanol. However, when high rank bituminous coals, which contain smaller amounts of oxygen, are utilized, the oxygen required can instead be derived from $CO_2$ by the in situ calcination of limestone used for partial desulfurization, or by the addition of water. When so employed, the addition of limestone serves three functions: (1) it removes sulfur from the coal, directly producing CaS, (2) it increases the production of carbon, and (3) it provides the oxygen required for the conversion of carbon to methanol.

Another advantage of the process of this invention, as compared with that described in the aforesaid parent application Serial No. 54,610, is that in the latter process, about 20% of the heating value of the bituminous feed coal is produced as a hydrogen-rich co-product gas. This hydrogen-rich gas is a valuable fuel (or a feedstock for the production of pure hydrogen) and should easily demand a minimum co-product price of $2.00/million BTU. However, unless the hydrogen-rich gas can be used in the vicinity of the carbon black-producing plant, it may be difficult to transport it, even if gas pipelines are available in the immediate vicinity. As of the present date, gas transmission by pipeline is usually limited to natural or substitute natural gases containing little or no free hydrogen.

It is true that the Gas Research Institute (GRI) in the United States has reported that the transmission of natural gas containing up to 10% hydrogen may be feasible with little addition in cost. However, this has yet to be put into practice. Furthermore, if a gas line is not available, to construct one could significantly increase the cost of the hydrogen-rich co-product to a user, especially if the user were some distance from the gas-generating plant. On the other hand, where the co-product is liquid methanol it can be readily transported as inexpensively as oil.

Much thought has been given to converting cheap remote gas to an easily transportable fuel. Just as carbon black can be stored and shipped as a solid fuel, so can methanol be stored and shipped as a liquid fuel. Gas, on the other hand, cannot be readily shipped and stored as a gas. The Electric Power Research Institute (EPRI) in the United States has recognized the value of converting gas from the gasification of coal to methanol in an integrated power plant because methanol can be more readily stored than gas. By the same reasoning, preparation of the liquid slurry fuel of this invention imparts the same storage and transportability properties.

For a large plant processing 25,000 tons/day of a lignite coal and producing 8100 tons/day of carbon black and 5400 tons/day of methanol, it is estimated that total plant investment would be of the order of 800 million dollars. (See Grohse, E. W. and Steinberg, M. "Economical Clean Carbon and Gaseous Fuels from Coal and Other Carbonaceous Raw Materials", Brookhaven National Laboratories Report BNL 40485, November, 1987, for the estimated capital costs of the hydropyrolysis/methane pyrolysis plants; an additional 200 million dollar investment is estimated for the methanol conversion facility. With a lignite coal feed (at an assumed cost of $10.00/ton), the selling price of the carbon black/methanol slurry fuel product in order to provide a 10% return on investment after taxes and depreciation would be about $2.25/million BTU ($13.50/barrel of fuel oil equivalent). If the capital requirements were doubled, the carbon/methanol product would have to be priced at about $3.50/million BTU or $21.00/barrel of fuel oil equivalent for the same return.

These fuel prices are in line with present prices of fuel oil used in oil-fired power plants. Thus, the carbon-methanol product of the present invention is an immediately competitive fuel for oil-fired plants, which may be prepared from indigenous reserves. Since it is pollutant free, the new product is also competitive with coal as a power plant feedstock, on environmental grounds. Its use eliminates the necessity for stack gas scrubbing, which ordinarily adds about one-third more capital investment to the cost of high sulfur coal- or high sulfur oil-fired power plant.

Another important advantage of the carbon black-methanol slurry fuels produced in accordance with the present invention is that these fuels have better properties than either of their two constituents. Although carbon black is a burnable fuel, its main disadvantage is that its volatility is negligible. Carbon black must therefore be ignited at a considerably higher temperature than say, a high volatile bituminous coal. However, if methanol is mixed with the carbon, the methanol provides the volatility and the slurry fuel readily ignites.

Conversely, methanol alone is a readily burnable fuel; however, its main disadvantage is that it has a very low energy density. For example, compared to oil or gasoline, it has only approximately one-half of the volumetric heating value of either of the latter fuels. However, in combination with carbon, having a specific gravity 2.5 times that of methanol, stable, pumpable non-polluting slurry fuels are readily produced having energy densities approximating those of gasoline or oil. Furthermore, the addition of methanol to, or the co-usage of carbon-methanol slurry fuels with, present "cleaned coal"—water slurry fuels, would solve the freezing problem presently of concern with the latter, since methanol lowers the freezing point of coal-water mixtures. The mutual enhancement of methanol and carbon as a combination fuel mixture is thus ideal.

In summary, the process and product of this invention are ideal in terms of (1) energy conservation, (2) environmental considerations, (3) economics, and (4) fuel properties, applicability, storage, and transportability.

PREFERRED EMBODIMENTS OF THE INVENTION

The process of the present invention may be illustrated by the following overall stoichiometric reaction employing a typical lignite coal as the feedstock:

$$CHO_{0.8}O_{0.2} = 0.8\ C + 0.2\ CH_3OH \tag{I}$$

(Moisture-free lignite coal)

By utilizing lignite coal having an optimum empirical formula of $CH_{0.8}O_{0.2}$, a product slurry comprising 60% by weight carbon black and 40% by weight methanol is produced.

To effect the foregoing net reaction, a three-step process is utilized, employing an initial, exothermic hydrogasification or hydropyrolysis step (Step 1), followed by an endothermic methane decomposition or pyrolysis step (Step 2), and a final exothermic methanol synthesis step (Step 3). The successive steps are presumed to be carried out under substantially equilibrium limited exit gas conditions, as represented in FIGS. 1 and 2, for example.

In order to design a practical process in accordance with the present invention, it is a priori necessary to specify the effluent gas pressures and temperatures for the three reactors (nominally 50 atmospheres and 800° C., 1100° C. and 260° C., respectively), from which the corresponding equilibrium compositions of the three effluent gases can be determined as discussed below (e.g., from FIGS. 1 and 2). It is further necessary a priori to specify the pressure and temperature of the gas leaving the methanol condenser (nominally 50 atmospheres and 0° to 50° C.).

With the four effluent gas temperatures thus specified, the hydrogen-to-oxygen (H/O) ratios of the corresponding gas streams can be determined by iterative application of the material balances around each of the three reactors and around the methanol condenser. As can be readily established, the H/O ratio of the gas leaving the hydropyrolyzer, those of the gases entering and leaving the methane pyrolyzer, and those of the gases entering and leaving the methane condenser are all identical, neglecting slight changes which might occur during desulfurization.

Figure 1:
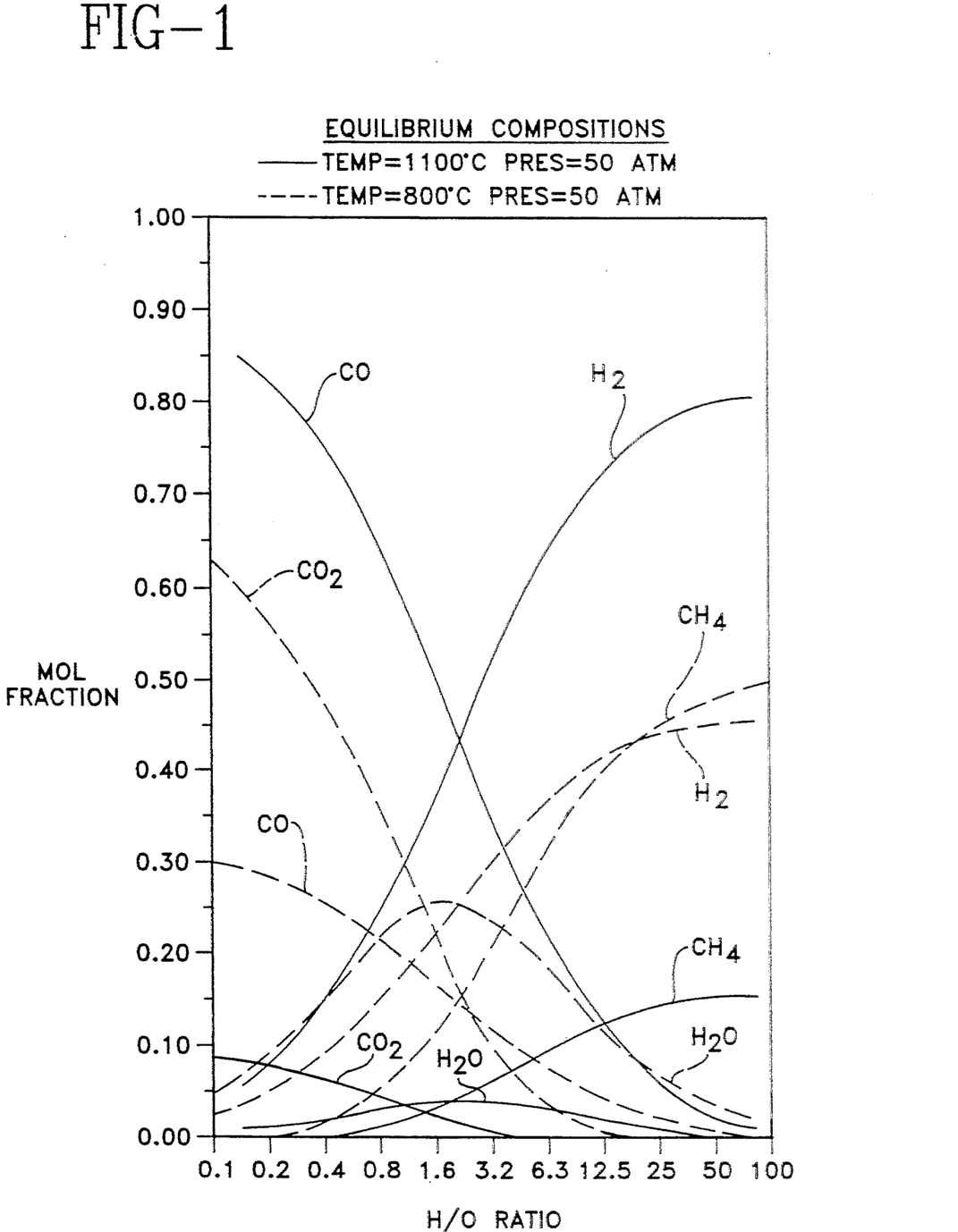
FIG. 1 is a graph of the equilibrium concentrations of hydrogen, methane, water, carbon monoxide, and carbon dioxide in the ternary C—H—O system at 50 atmospheres and 800° C. and 1100° C., representative of the exit gas streams from the hydropyrolyzer and methane pyrolyzer, respectively.
Figure 2:
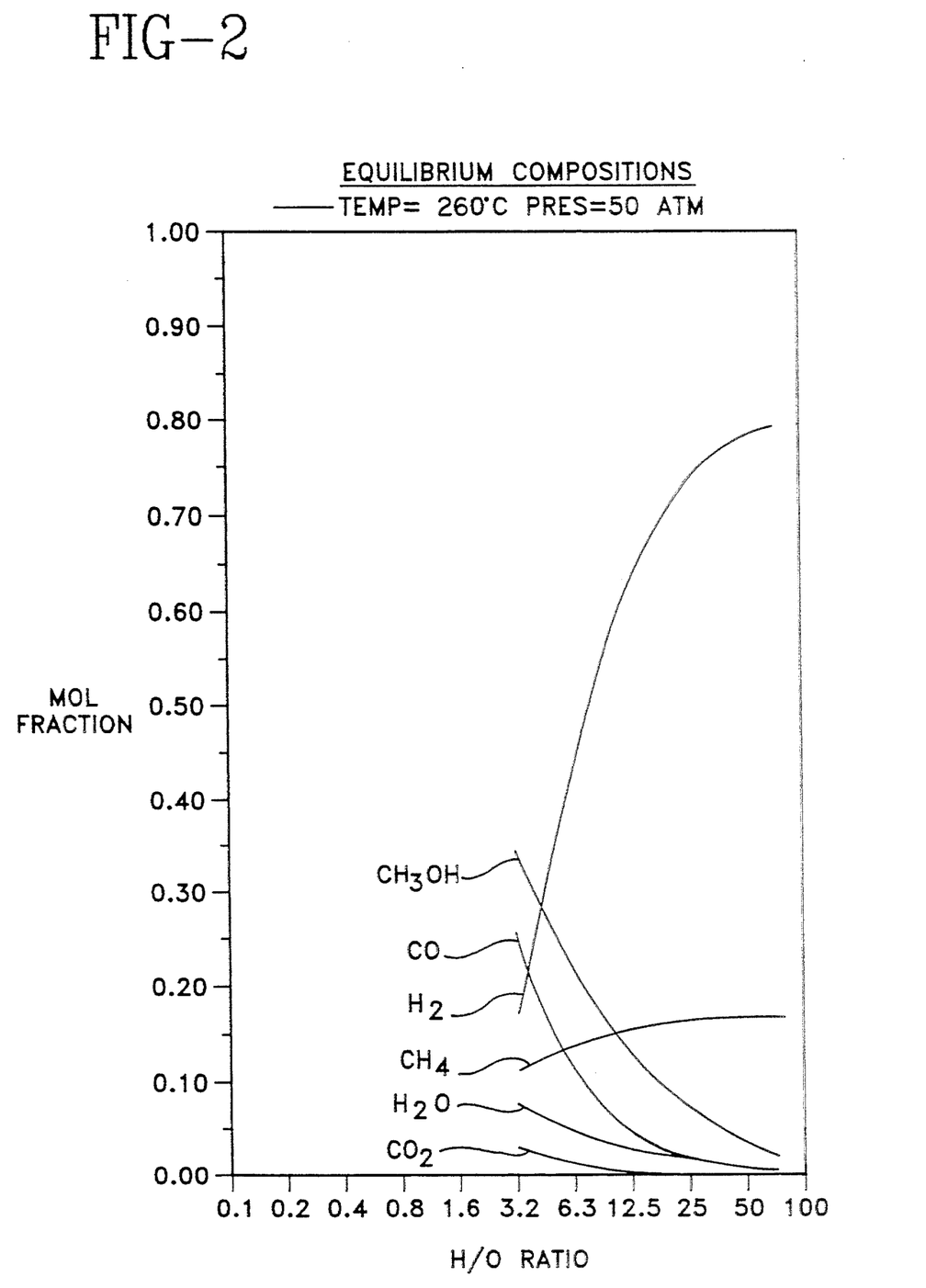
FIG. 2 is a similar graph of the equilibrium concentrations in the ternary C—H—O system at 50 atmospheres and 260° C., representative of the exit stream from the methanol converter.

For the hydropyrolysis and methane pyrolysis steps, by following the equilibrium gas compositions presented in FIG. 1 for the ternary system C—H—O at 50 atmospheres and 800° C. and 1100° C,. respectively, for the above steps, the concentrations of the five major components ($CH_4$, $CO$, $H_2$, $H_2O$, and $CO_2$) comprising an equilibrium gas can be determined for any specified overall H/O gas ratio. At the pressure and temperature conditions for the above reaction steps, the concentration of methanol is negligible.

Similarly for the methanol synthesis step performed at 50 atmospheres but at 260° C., FIG. 2 presents the equilibrium compositions of the above five constituents plus that of methanol in an equilibrium gas leaving the methanol converter, based upon the feed to the latter comprising an equilibrium gas from the methane converter, after precooling and final desulfurization.

Success of the overall process is assured by recycling the hydrogen-rich gas stream (formed during the methane pyrolysis step and modified during the methanol synthesis and condensation steps) and by maintaining optimum temperatures for the gases leaving the three reactors and the methanol condenser. The above-cited nominal effluent gas temperatures, although not necessarily optimum, demonstrate economic feasibility of the process of the invention. For example, at the aforementioned reactor effluent gas temperatures of 800° C., 1100° C., and 280° C., respectively, for steps 1, 2, and 3, and an effluent condenser gas temperature of 50° C., using a moisture-free high volatile bituminous coal as feedstock with an H/O ratio of approximately 10, the H/O ratios of the three reactor effluents are identically 73 and that of the gas leaving the condenser is 158, neglecting the effect of limestone used for desulfurization.

As disclosed in connection with the aforesaid parent application, the use of high H/O ratios in the respective gas streams provides nearly the maximum carbon conversion efficiency (and, hence, the maximum yield of particulate carbon product) as well as requiring nearly the minimum rate of recycle gas to the hydropyrolysis reactor (and hence, nearly the minimum gas compression cost, an important operating cost consideration). The H/O ratios in the gas streams are at least equal to, and preferably are in excess of, that of the dry carbonaceous feedstock used in the process, (typically about 10 for bituminous coal, 4 for lignite coal and 2 for biomass).

By deoxygenating the process gas streams by conversion to methanol, the process of this invention additionally provides a new and valuable co-product, methanol, which can be used by itself as a versatile chemical commodity or as a non-polluting fuel, or in which the carbon black co-produced may be slurried to produce a high energy density non-polluting liquid fuel.

Energy and material balances are maintained by running both the hydropyrolysis and methane pyrolysis reactors essentially isobarically, and transferring the exothermic heat liberated in Step 1 to provide the endothermic heat required in Step 2. Preferably, heat transfer between the feedstock and the respective gaseous media is effected in a moving bed reaction system, utilizing a particulate refractory material heat transfer medium. Finally, the process hereof effects a high degree of conversion of even relatively low concentrations of carbon monoxide present in the effluent streams from either Step 1 or Step 2, to methanol, utilizing currently available commercial catalysts.

The present process may be carried out with any suitable carbonaceous feedstock or mixtures thereof, preferably those having empirical formulas approximating $CH_{0.05-2.0}O_{0.05-1.0}$. Use of the process is particularly advantageous with bituminous ($CH_{0.8}O_{0.1}$) and lower rank coals such as lignite ($CH_{0.8}O_{0.2}$). Such materials contain sufficient hydrogen and oxygen in their molecules to produce relatively high concentrations (up to 30%, preferably from about 1 to 15%, by volume) of carbon monoxide in Step 1 of the process, resulting in the formation of sufficient quantities of methanol in Step 3 of the process.

When bituminous coal is used by itself, three products are produced, namely: carbon, methanol, and a gas usually containing primarily hydrogen:

$$CH_{0.8}O_{0.1} = 0.9\ C + 0.1\ CH_3OH + 0.2\ H_2 \quad \text{(IIA)}$$

(Moisture-free bituminous coal)

As indicated below, when bituminous coal is utilized to produce a maximum amount of methanol and, hence, a minimum amount of co-product gas, it is necessary to co-feed 0.2 moles of water per mole of carbon in the bituminous coal being fed. This water can be in the form of moisture already contained in as-received coal (11% would be required on an ash-free basis) or else the water can be added separately if the contained moisture is insufficient. (A minimal draw-off of co-product gas is required in any case in order to prevent build-up of inert constituents such as nitrogen introduced with the feedstock.) In this case, disregarding inert constituent draw-off, the stoichiometry of the overall reaction is as follows:

$$CH_{0.8}O_{0.1} + 0.2\ H_2O = 0.7\ C + 0.3\ CH_3OH \quad \text{(IIB)}$$

(Moisture-free bituminous coal)

The judicious addition of carbon dioxide during hydrogasification of bituminous coal (e.g., as generated when limestone is used for desulfurization) also increases the production of methanol, to a lesser extent than by the addition of water, but also with a lesser decrease in the production of carbon:

$$CH_{0.8}O_{0.1} + 0.05\ CO_2 = 0.85\ C + 0.2\ CH_3OH \quad \text{(IIC)}$$

(Moisture-free bituminous coal)

Biomass (wood, paper, or municipal solid waste), having the approximate empirical formula $CH_{1.44}O_{0.66}$, can also be used as a co-feedstock with bituminous coal. When so employed, the following reaction takes place:

(II D)    $CH_{0.8}O_{0.1} + 0.33\ CH_{1.44}O_{0.66} = 1.01\ C + 0.32\ CH_3OH$
(Moisture-free bituminous coal)    (Biomass)

The empirical composition of wood on a dry, CHO basis is $CH_{1.44}O_{0.66}$. Paper, being derived from wood, is considered to have essentially the same empirical composition. Municipal solid waste (MSW) is regarded as having the following approximate composition:

| MSW | Wt. % |
| --- | --- |
| C | 25 |
| H | 3 |
| O | 21 |
| S, N | 1 |
| Ash | 50 |
| Moisture: 50% | |
| Net Heating Value: 5,000 BTU/lb | |
| (Dry Basis) | |

The above composition corresponds to the empirical formula $CH_{1.43}O_{0.63}$ (vs. $CH_{1.44}O_{0.66}$ for paper) which should not be surprising in light of the high paper content of MSW.

By itself, using the present process, biomass would produce predominantly carbon, very little methanol, and water. Using the above general formula for biomass ($CH_{1.44}O_{0.66}$), the following reaction takes place:

$$CH_{1.44}O_{0.66} = 0.94\ C + 0.06\ CH_3OH + 0.60\ H_2O \quad \text{(IIE)}$$

(Biomass)

By the addition of a carbon monoxide separator, substantial carbon monoxide can be produced as a gaseous co-product, along with additional methanol and much less carbon:

$$CH_{1.44}O_{.66} = 0.34\ C + 0.36\ CH_3OH + 0.3\ CO \quad \text{(IIF)}$$

(Biomass)

When biomass is used as the primary carbonaceous feedstock it is desirable (because of its high oxygen content) to add a hydrogen-rich raw material as a co-feedstock. For example, methane (natural gas) may be conveniently utilized for this purpose, as follows:

$$CH_{1.44}O_{0.66} + 0.3\ CH_4 = 0.64\ C + 0.66\ CH_3OH \quad \text{(IIG)}$$

(Biomass)

Alternatively, scrap oil or scrap rubber from tires can be used as co-feedstocks with biomass; these materials have approximate empirical formulae of $CH_{1.7}$ and $CH_{1.33}$, respectively:

| | |
|---|---|
| (II H) | $CH_{1.44}O_{0.66}$ + 0.71 $CH_{1.7}$ = 1.05 C + 0.66 $CH_3OH$ |
| | (Biomass) (Scrap Oil) |
| (II I) | $CH_{1.44}O_{0.66}$ + 0.90 $CH_{1.33}$ = 1.24 C + 0.66 $CH_3OH$ |
| | (Biomass) (Scrap rubber) |

From the preceding it will be seen that a wide variety of carbonaceous materials (solid, liquid, or gaseous) may be employed as feedstocks to the process of the present invention. Such materials include coals of any rank, such as anthracite, bituminous sub-bituminous, and lignite; peat, char,oil, natural gas, wood, paper, municipal solid wastes, scrap rubber, scrap plastics, and the like-that is, virtually any carbonaceous material, from which valuable non-polluting fuels and/or commodity chemicals can be economically produced.

Figure 3:
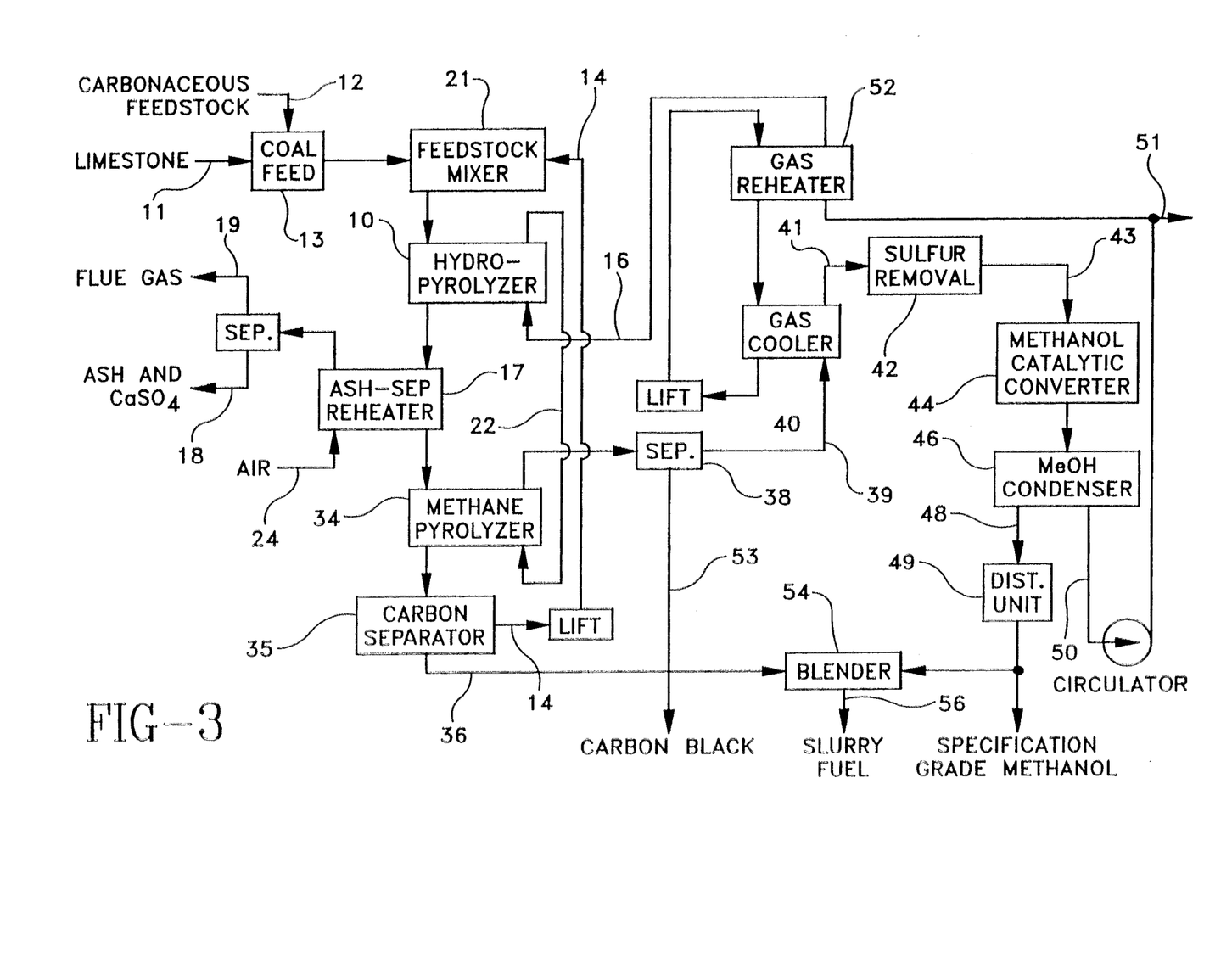
FIG. 3 is a simplified flow sheet illustrating a currently preferred embodiment of the process.

A particular technique for carrying out the process of the present invention is schematically illustrated in FIG. 3:

Step 1—Hydropyrolysis

As shown in the drawing, a hydropyrolysis reactor 10 is provided defining a hydropyrolysis zone into which is passed a carbonaceous material feedstock of a type previously described, such as a stream of bituminous or lignite coal 12. Any co-feedstock, e.g., steam or water, methane, wood, or the like, is added to stream 12, and the total carbonaceous feedstock is thereafter admixed with a limestone feed stream 11 within a feedstock preparation zone 13. In the preparation zone, the coal is initially comminuted to a particle size range of the order of about 3-30 millimeters. When coal is used as the feedstock, it may be used either wet or dry and may be added in admixture with the limestone. If preheated and/or dried prior to entering the hydropyrolyzer, the flue gas stream 19 from the ash separator/reheater 17 described below may be used as the source of heat.

The limestone stream 11 is added to coal feed stream 12 in order to convert as much as possible of the sulfur present in the latter stream to calcium sulfide in hydropyrolyzer 10. The calcium sulfide is thereafter oxidized during reheating in separator/reheater 17 to calcium sulfate, and the latter is removed together with unreacted calcium oxide in the effluent ash stream 18.

Fired alumina pellets or spheres, hereinafter called spheres, of the type used in moving- and fluidized-bed reactors and the like, having average particle diameters within the range of about 2 to 12 millimeters, typically 3 millimeters, are used in the moving beds 10, 34, 40 and 52 depicted in FIG. 3 as transportable heat transfer media. In one mode of operation of the hydropyrolysis reactor 10, these spheres are recycled via stream 14, admixed with the coal and limestone feed in a mixer 21, and thereafter fed into the hydropyrolysis reactor 10. For a plant processing 25,000 tons per day of bituminous coal, the total solids flow rate entering reactor 10 (which may be a multiplicity of smaller reactors) may be as high as 7 tons per second.

The feedstock/alumina/limestone mixture descends by gravity through the hydropyrolysis reactor countercurrent to the flow of a hydrogen-rich gas stream 16, which typically enters the bottom of the reactor, contacts the carbonaceous solids and reacts with the same while ascending through the reactor at a typical average superficial velocity of approximately 3 feet per second (0.9 meters per second).

In the hydropyrolysis reactor 10, an exothermic reaction occurs between the carbonaceous material and the hydrogen containing gas which releases thermal energy of about 18 kilocalories per gram mole of methane produced. The exothermic heat of reaction and the excess sensible heat of the entering gas heat the contents of the hydropyrolysis reactor, which is removed therefrom as the sensible heat of a solid effluent 15 (comprising a mixture of the particulate refractory material and ash; also calcium sulfide and calcium oxide if limestone is used) and the sensible heat of a methane-rich product gas stream 22. The rate of circulation of the particulate refractory material within the hydropyrolysis reactor relative to the rate of feed of the carbonaceous feedstock 12, is controlled so as to maintain desired temperature conditions within hydropyrolysis reactor 10 for optimum production of methane from the feedstock.

The required residence time of the carbonaceous material in hydropyrolysis reactor 10 depends upon many factors, including the type of feedstock being processed and the desired approach to equilibrium conversion of the feedstock. Economics or local conditions may dictate use of a plurality of smaller hydropyrolysis reactors in parallel. In order to obtain a high yield of methane during the hydropyrolysis, the residence time of the carbonaceous material is generally within the range of about 3 to 60 minutes, typically about 10 to 15 minutes. As used herein, the term "residence time" refers to the average time the carbonaceous material is maintained within the hydropyrolysis reactor in contact with the hydropyrolysis gas 16, any co-feedstock, and the particulate refractory material in stream 14.

During operation under substantially steady state conditions, operating temperatures in the hydropyrolysis reactor 10 are basically controlled by the relative rates of flow of the solids and gases passed therethrough. In practice, the gas flow rate is regulated by the feedstock flow rate. Temperatures in the methane pyrolysis reactor 34 are essentially controlled by the temperature of the solids leaving the hydropyrolysis reactor 10 and the heat input to the ash separator-reheater 17, which heat may be provided by means of fuel (and air) fed externally to the reheater or by providing for incomplete conversion of the carbonaceous feedstock fed to the hydropyrolysis reactor and providing an air stream 24 to combust the unconverted carbon. In either case, reheating of the alumina provides for simultaneous oxidation of calcium sulfide being discharged from the hydropyrolysis reactor, presuming the use of limestone for partial desulfurization. With certain feedstocks, reheating of the refractory material may not be required. A suitable outlet gas temperature range from hydropyrolysis reactor 10 is about 600° to 1200° C., typically about 800° C.

The hydropyrolysis reactor 10 as well as the methane pyrolysis reactor 34 and the methane converter 44 are desirably maintained at substantially isobaric conditions, preferably within a range of about 10 to 200 atmospheres, approximately 50 atmospheres being a nominal design pressure considered suitable for the efficient and economic extraction of the carbon moiety of most solid carbonaceous materials available in substantial quantities at competitive prices. Within the system itself there are small departures from isobaric operation caused by bed pressure drops and other frictional losses.

In accordance with thermodynamic equilibria, conditions of relatively higher pressure and lower temperature favor the formation of methane from carbon and hydrogen, while conditions of relatively lower pressure and higher temperature favor the decomposition of methane to carbon and hydrogen. On this basis, reaction temperatures as low as possible within the foregoing range, consistent with the requirements of kinetics, combined with a pressure as high as possible within the foregoing range, are desirably maintained in the hydropyrolysis reactor. At the same time, reaction temperatures as high as possible, consistent with materials of construction limitations, are desirably maintained in the methane pyrolysis reactor. However, both reactors as well as the methanol converter 44 and partial condenser 46 are operated at substantially isobaric conditions in order to minimize gas recirculation costs which otherwise might make the process uneconomic.

The effect of different combinations of pressure and temperature upon reaction rates must also be considered in order to achieve practical rates of production. Consequently, the hydropyrolysis reactor 10 is designed to operate under conditions of temperature and residence time that will yield exit gas streams whose compositions are determined by temperature, pressure, and the atomic hydrogen-to-oxygen (H/O) ratio. In addition, practical considerations such as materials of construction and the cost of re-compression limit the extremes of pressure and temperatures that are economically feasible. For these reasons, it is preferred to operate under substantially isobaric conditions, which minimize re-compression costs, and provide for reasonable temperature and pressure conditions and residence times required for economic commercial operation.

Preferably, the hydrogen-rich, methane-lean and carbon monoxide-poor gas stream introduced into the hydropyrolysis reactor contains, by volume, about 50 to 90% hydrogen, 0.5 to 30% carbon monoxide, 5 to 30% methane, and 0 to 10% water plus carbon dioxide. Employing the foregoing reaction conditions, the methane-rich exit gas stream 22 from the hydropyrolysis reactor contains, by volume, about 20 to 60% methane, 25 to 60% hydrogen, 0.5 to 15% carbon monoxide, and 1 to 40% water plus carbon dioxide.

Step 2—Methane Pyrolysis

The methane-rich gas stream 22 removed from the hydropyrolysis reactor is fed directly into a methane decomposition or methane pyrolysis reactor 34. On the other hand, the effluent 15 removed from the hydropyrolysis reactor is initially passed through the separator/reheater 17 in which an ash stream 18 and a flue gas stream 19 are separated, and from which the remaining refractory heat transfer material stream 20 is recovered. Stream 20 is re-heated prior to entering the methane pyrolysis reactor, and is thereafter fed by gravity therethrough. The methane-rich gas stream 22 is passed countercurrent to the descending moving bed of particulate refractory material 20 in reactor 34. The total thermal energy stored in stream 20 provides the endothermic energy requirement for thermal decomposition to carbon and hydrogen (also about 18 kilocalories per gram mole of methane).

A particulate carbon stream 36 is separated from the mass of particulate refractory material removed from reactor 34 in a separator 35 before returning the particulate refractory material stream 14 to the hydropyrolysis reactor. Carbon black is also removed from gas stream 37 employing a gas-solids separation facility 38.

The required residence time of the reaction mixture in methane pyrolysis reactor 34 will basically depend upon temperature, pressure, and the desired approach to equilibrium disassociation of the methane in the entering methane-rich gas stream 22. Thus, the residence time may vary through a range between about 2 and 40 seconds, typically of the order of about 6 seconds. In this context, the "residence time" is the duration of contact of the methane-rich gas 22 with the moving bed of particulate refractory matter 20 gravitating through the methane pyrolysis reactor 34.

The operating temperatures within the methane pyrolysis reactor 34 are basically controlled by regulation of the relative flow rates of the solids and gases passed therethrough and the heat input to the ash separator reheater 17. A suitable temperature of the exit gas stream 37 lies in the range of about 800° to 1400° C., typically about 1100° C.

The temperature of the gas leaving the methane pyrolysis reactor 34 is at all times maintained at a substantially higher value than that of the gas leaving the hydropyrolysis reactor 10. As mentioned above, the separator/reheater 17 heats the particulate refractory material 20 in order to maintain the desired temperature of the gas leaving the methane pyrolysis reactor. Preheated air for the combustion in reheater 17 can advantageously be provided by heat exchange of an ambient air stream 24 with the hot ash stream 18 removed from the separator/reheater 17 and with the hot particulate carbon streams recovered from the carbon black separators 35 and 38. The hot flue gas stream 19 leaving separator/reheater 17 can, in turn, advantageously serve to preheat and dry the feedstock 12 if desired.

As indicated above, the hydropyrolysis reactor 10, the methane pyrolysis reactor 34, and the associated separators 17, 35 and 38 are desirably operated as a closed system under substantially isobaric conditions, preferably within a range of about 10 to 200 atmospheres, and typically at about 50 atmospheres. Again, it will be understood that there are slight departures from the nominal design pressure within the system caused by bed pressure drops and other frictional losses.

Consistent with the foregoing, the methane-rich stream 22 fed into methane pyrolysis reactor 34 is converted therein to a hydrogen-rich and comparatively carbon monoxide-rich exit stream 37 containing, by volume, about 50 to 90% hydrogen; 0.5 to 30% CO; 5 to 30% methane; and 0 to 10% water plus $CO_2$.

Step. 3—Methanol Conversion

In a preferred version of the present invention, carbon monoxide and hydrogen in stream 37 are converted to methanol in methanol catalytic converter 44 following recuperative cooling and essentially complete desulfurization. The hydrogen-rich, and comparatively carbon monoxide-rich stream 38 is first recuperatively cooled in a cooler 40 to temperatures of about 200°-300° C., typically about 260° C., to facilitate the catalytic conversion. Desulfurization is completed in sulfur removal facility 42 (which may include a final sulfur guard bed prior to the entry of feed stream 43 into converter 44. The sulfur guard may contain one or more reactant/adsorbents (e.g., zinc oxide, activated charcoal, and the like) in order to insure the removal of all potential sulfur poisons from the gas stream 41 prior to allowing the latter to contact the methanol-forming catalyst.

In the process illustrated in FIG. 3, the greater proportion of the sulfur entering with the feedstock, nominally 90%, is removed by the co-feeding of limestone. (Note that $CO_2$ generated by calcination of the limestone enhances the carbon monoxide concentration in the gas leaving the methane decomposition reactor, thereby providing for the additional co-production of methanol.) Most of the remaining desulfurization required is preferably effected by means of a dry hydrogen sulfide-removal process operable at approximately the temperature of the methanol converter. Alternatively, a wet $H_2S$-removal process may be utilized, in which case stream 39 is first cooled below the optimum methanol conversion temperature and then subsequently reheated prior to entering converter 44, final desulfurization again being accomplished by means of a sulfur guard bed.

The partial conversion of stream 43 to methanol may be effected employing commercially available catalysts such as described in the technical literature. (See the aforesaid excerpts from *Industrial Chemicals*, Faith, Keyes and Clarke, 4th edition, pp 524–529 (1975) and from the *Encyclopedia of Chemical Technology*, Kirk and Othmer, 3rd Edition, Vol. 15, pp. 398–415 (1981). So-called low pressure catalysts comprising mixed oxides of zinc and copper, operable at about 200°–300° C. and 50 to 100 atmospheres and available from ICI Ltd., may suitably be utilized inasmuch as essentially isobaric operation, typically at about 50 atmospheres, is desired in order to minimize gas recirculaton costs.

The gaseous product stream 45 exiting from catalytic converter 44, if fed with desulfurized, hydrogen-rich gas from the methane pyrolyzer 34, contains, by volume, about 1 to 30% methanol, 10 to 25% methane, 0 to 20% carbon monoxide, 25 to 90% hydrogen, 0 to 10% water vapor, and 0 to 5% carbon dioxide. After condensation in condenser 46, a methanol/water liquid product stream 48 is recovered. Most of the residual gas stream 50 (hydrogen-rich and now carbon monoxide-lean) is recycled to the hydropyrolysis reactor 10. The remainder of the latter stream constitutes a co-product or purge gas stream 51 containing the excess hydrogen and all of the inert constituents (in particular, nitrogen) entering with the carbonaceous feedstock, which otherwise would accumulate in the recirculating gas stream 16.

The condensate stream 48 contains, by weight, about 75 to 100% methanol and 0 to 25% water. This stream may be fractionated in distillation unit 49 (suitably by steam heat as may be generated via flue gas stream 19) to separate a pure specification-grade methanol product or, as shown in the drawing, be directly admixed with the particulate carbon product streams 36 and 53 in blender 54 to provide a high energy density slurry product 56, nominally containing approximately 60 weight % carbon and 40 weight % methanol. This slurry product is pollutant-free, has a heating value of about 120,000 BTU/gallon, and may be directly utilized as a fuel.

Based upon the gas stream from the methane pyrolyzer 34 being (partially) catalytically converted to methanol, after cooling and desulfurization, the process gas stream 50 leaving partial condenser 46 contains, by volume, about 40 to 90% hydrogen, 0 to 40% carbon monoxide, 10 to 30% methane, 0 to 10% carbon dioxide, 0 to 3% methanol, and 0 to 1% water vapor. The methanol and water concentrations depend upon the final temperature of condensation (nominally between 0° C. and 50° C., as in the above example. Most of the process gas stream 50 is recuperatively reheated via gas heater 52 and then recycled as the hydrogen-rich feed gas stream 16 to the hydropyrolysis reactor 10. The remainder is removed as the co-product or purge gas stream 51.

Heat Exchange

Thermal energy released in the hydropyrolysis reactor 10 in Step 1 (by the exothermic reaction of hydrogen with carbon to form methane) is transferred to the endothermic gas-phase thermal decomposition reaction in the methane pyrolysis reactor 34 (Step 2) by the use of the particulate refractory material referred to hereinabove. The latter acts as a heat transfer medium, moving successively through the hydropyrolysis reactor 10 and the methane pyrolysis reactor 34 as a dense bed countercurrent to the bulk movement of the gas streams within the respective reactors.

The refractory material must, of course, be substantially unaffected by the varying temperature conditions utilized in the reaction systems. It must be dense and mechanically strong to withstand the rigors and shock of tumbling encountered during its transport as a moving bed through the reactors, during its separation from ash and from the particulate carbon product in separators 17 and 35, and during its transport between the reactors via solids-transport devices such as mass lift pressure conveyor systems of the type used in petroleum refineries and the like.

A major requirement, in addition to the ability to withstand temperature extremes and mechanical shock and to resist chemical action without deterioration, is that the refractory material have a greater specific gravity than any of the other solids encountered in the process (viz., the carbonaceous feedstock, the char and ash, and the particulate carbon). Solids separation on the basis of their differences in specific gravity and particle size, as in the well known method of elutriation, is thus facilitated.

A fired aluminum oxide ceramic of the type generally utilized in granular and pellet form in the refining of petroleum has been found useful as the particulate refractory heat transfer medium employed in this process. Materials of this general type which have high densities (for example, about 4 grams/cc), high melting points (about 2000° C.) and high specific heats (about 0.28 calories/gram/° C.) have been found particularly useful herein.

The carbonaceous feed will ordinarily be substantially diluted by the refractory heat transfer medium fed to the hydropyrolysis reactor 10, thereby lessening any tendency of the feedstock to agglomerate. Furthermore, the refractory flow rate must be sufficient to prevent fusion of the ash or char within separator/reheater 17 or within reactor 10. In a typical case employing alumina particles as the heat transfer medium and bituminous coal as the carbonaceous feedstock, the weight ratio of alumina and coal fed to the hydropyrolysis reactor 10 may be as much as 20:1, this ratio being determined by a heat balance between the heat transfer medium and the entering coal 12 and limestone 11, the entering gas stream 16, the exiting ash or char 18, and the exiting gas stream 22. In this manner, good heat transfer is obtained and, moreover, the possibility of agglomeration of the coal, which might otherwise impede efficient operation of the reactor, is minimized.

High swelling coals such as the Eastern bituminous coals are known to agglomerate in gasification procedures. The alumina particles minimize or prevent agglomeration of the coal, and the high melting temperature of the alumina minimizes the possibility of its reaction with the ash formed. Not all particulate heat transfer media preclude agglomeration in the same manner; sand, for example, has a relatively low melting point and would tend to react with the ash formed in the hydropyrolysis reactor.

Alternative Operations

As indicated hereinabove, it is preferred to carry out Steps 1 and 2 of the process of the invention employing countercurrent moving bed operations, i.e., the particulate carbonaceous feedstock and the heat transfer medium flow countercurrent to the hydrogen-rich gas stream in the hydropyrolysis reactor 10, and the methane-rich gaseous stream formed therein flows countercurrent to the particulate heat transfer medium in the methane pyrolysis reactor 34. Countercurrent flow maximizes heat and mass transfer as well as kinetic driving forces during these operations. However, it should be understood that virtually any type of solids-gas reactor system incorporating, for example, multistage fluidized bed reactors, fixed bed reactors, or entrained flow reactors may be employed to carry out the process of the present invention.

As described above, it is also preferred in the practice of this invention to utilize the hydrogen-rich, carbon monoxide-rich gas stream 37 from the methane pyrolysis reactor 34 as the make gas (after desulfurization) for the methanol catalytic converter 44. Since the temperature of gas stream 37 is substantially higher than the temperature of the methane-rich stream 22 removed from hydropyrolysis reactor 10 (e.g., of the order of 1100° C. versus 800° C.) stream 38 generally has a higher carbon monoxide content (of the order of about 0.5 to 30% by volume, as contrasted with a carbon monoxide content of about 0.5% to 15% by volume in stream 22). Conversion of the gas stream containing a higher carbon monoxide content assures higher methanol conversions.

Alternatively, however, it is within the scope of this invention to utilize the methane-rich stream 22 from the hydropyrolysis reactor as the make gas for the methanol synthesis, if desired in accordance with particular process requirements. In its broadest sense, the methanol conversion may be carried out employing either gas stream containing, by volume, about 25 to 90% hydrogen, 5 to 60% methane, 0.5 to 30% carbon monoxide, 0 to 30% water, and from 0 to 10% carbon dioxide.

Auxiliary Operations

Although not specifically illustrated in FIG. 3, other conventional operations are utilized in connection with the process illustrated therein. Hence, the ash stream 18 and carbon black product stream 36 are both cooled to near ambient temperature, and the gaseous co-product stream 51 or a portion thereof, may be combusted as needed to provide additional thermal energy to compensate for heat losses from the system and to provide for the relatively higher temperatures required to optimize conditions in the endothermic reaction in Step 2. As noted above, the air stream 24 required for the combustion is preheated by use in certain selected cooling operations, as by cooling the ash stream 18 and the particulate carbon product streams 36 and 53. Also, the flue gas 19 may be employed to heat and dewater the initial feedstock and to generate process steam.

Additionally, the separator/reheater 17 which, during routine continuous operation of the integrated process, is used to provide the heat required for the high temperature operation of the methane pyrolysis reactor, is advantageously used during initial start-up to bring the reactors to operating temperatures.

Those skilled in the art will appreciate the economic potential of such dual use of items of auxiliary equipment. During start-up, natural gas may be fed to the methane pyrolysis reactor 34 in order to produce hydrogen prior to introducing the carbonaceous feedstock into the hydropyrolysis reactor 10. Subsequently, the hydrogen present in the carbonaceous feedstock provides an excess of the hydrogen required for routine operation of the process. Thus, the process of the present invention contrasts markedly with prior art procedures.

It will be understood that various changes may be made in the foregoing example without departing from the scope of the present invention. For example, as noted above, while countercurrent flow, moving-bed reaction systems have been exemplified, fluidized-bed or other types of reactors can be used in reaction steps 1 and 2 hereof, if desired. Also, it should be understood that certain materials can be added, including catalysts to improve the kinetics of the hydropyrolysis and methane pyrolysis reactions, without departing from the scope of the invention. Similarly, a variety of reactor types and catalysts can be used for the production of methanol in reaction step 3.

Accordingly, the preceding description is intended as illustrative only, and the scope of this invention should be determined by construction of the claims appended hereto.

We claim:

1. A continuous, integral cyclical process for the conversion of a bituminous or lignite coal feedstock to particulate carbon and methanol products, used separately and/or in combination as a pollutant-free liquid slurry product or fuel, which comprises:
   (a) reacting the feedstock in a first stage hydropyrolysis reaction zone maintained at a pressure within the range of from 10 to 200 atmospheres and at temperatures within the range of approximately 600° to 1200° C., with a hydrogen-rich gas stream containing, by volume, from about 5 to 30% methane, 50 to 90% hydrogen, 0.5 to 30% carbon monoxide, and 0 to 10% water plus carbon dioxide, to produce a methane-rich gas stream containing, by volume, from about 20 to 60% methane, 25 to 60% hydrogen, 0.5 to 15% carbon monoxide, and 1 to 40% water plus carbon dioxide;
   (b) decomposing the methane in the methane-rich gas stream in a second stage methane pyrolysis reaction zone, maintained at substantially the same pressure as the hydropyrolysis reaction zone in step (a) but at higher temperatures, ranging from 800° to 1400° C., to produce the particulate carbon product and a hydrogen-rich gas stream containing, by volume, from about 5 to 30% methane, 50 to 90% hydrogen, 0.5 to 30% carbon monoxide, and 0 to 10% water plus carbon dioxide;
   (c) passing the hydrogen-rich gas stream through a catalytic conversion zone maintained at substantially the same pressure as in the hydropyrolysis and methane pyrolysis zones, but at a lower temperature, ranging from 200° to 300° C., to catalytically convert the carbon monoxide, carbon dioxide and hydrogen contained therein to a methanol-rich, carbon monoxide-lean gas stream;

(d) separating the methanol product from the methanol-rich, carbon monoxide-lean gas stream, leaving a methanol-lean gas stream;

(e) separating and recovering the particulate carbon product and the methanol product separately or as a combined liquid slurry product;

(f) directly recycling at least part of the methanol-lean gas stream from step (d) to step (a) for further hydropyrolysis; and (g) removing any remaining portion of the methanol-lean gas stream from the process;

the temperatures and pressures in the respective reaction zones being so regulated as to maintain an atomic hydrogen/oxygen ratio in each of the hydrogen-rich and methane-rich gas streams in excess of 4.

* * * * *